Figure 1:
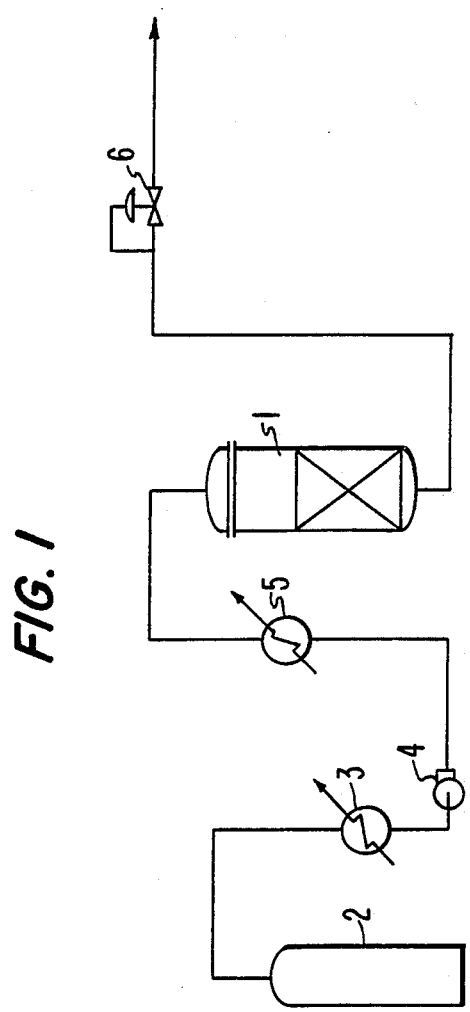

United States Patent [19]

Maeda et al.

[11] Patent Number: 4,978,752
[45] Date of Patent: Dec. 18, 1990

[54] CRYSTALS OF CEPHEM HYDROCHLORIDE

[75] Inventors: Yoshiharu Maeda; Yukio Mizuno, both of Osaka; Akira Nakatani, Hyogo; Mitsuhisa Yamano, Osaka, all of Japan

[73] Assignee: Takeda Chemical Industries, Ltd., Osaka, Japan

[21] Appl. No.: 274,976

[22] Filed: Nov. 22, 1988

[30] Foreign Application Priority Data

Dec. 4, 1987 [JP] Japan .................... 62-308351

[51] Int. Cl.$^5$ .................. C07D 501/46; A61K 31/545
[52] U.S. Cl. ..................................... 540/222; 514/206
[58] Field of Search .......................... 540/222

[56] References Cited

PUBLICATIONS

The Merck Index, pp. 270, 271, 272 (1983), Tenth Edition.

Primary Examiner—Nicholas S. Rizzo
Attorney, Agent, or Firm—Wegner & Bretschneider

[57] ABSTRACT

Crystals of 7β-[(Z)-2-(5-amino-1,2,4-thiadiazol-3-yl)-2-methoxyiminoacetamido]-3-(1-imidazo[1,2-b]pyridazinium)methyl-3-cephem-4-carboxylate hydrochloride or a solvate thereof, which are stable and improved in solubility in water, are useable for an excellent antibacterial agent.

10 Claims, 11 Drawing Sheets

SCE-2787(HCl)

CRYSTALS OF CEPHEM HYDROCHLORIDE

This invention relates to crystals of a cephem hydrochloride which is useful as an antimicrobial compound. More particularly, it relates to crystals of 7β-[(Z)-2-(5-amino-1,2,4-thiadiazol-3-yl)-2-methoxyiminoacetamido]-3-(1-imidazo[1,2-b]pyridazinium)-methyl-3-cephem-4-carboxylate [hereinafter referred to briefly as SCE-2787] hydrochloride [hereinafter referred to as SCE-2787(HCl)] or a solvate thereof.

SCE-2787 is a useful cephem compound disclosed in Japanese Kokai Tokkyo Koho No. 62-149682 (European Patent Application Laid-Open No. 203271), which has the formula (I) given below and shows good antimicrobial activity against gram-positive bacteria as well as gram-negative bacteria.

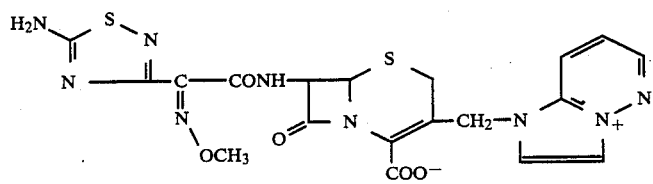

(I)

While SCE-2787 shows excellent antimicrobial activity, SCE-2787 has certain problems. Thus, it has been impossible to produce it in forms other than the amorphous form. The amorphous solid has unsatisfactory stability and, when stored under ordinary conditions for a long period, discolors and loses its purity (decrease in active ingredient content). For producing the amorphous solid in substantially pure form, troublesome purification steps are disadvantageously required.

As a result of their intensive investigations made to solve the above problems, the present inventors found that SCE-2787 can be obtained in the form of stable crystals and that it can be readily purified by crystallization. However, the thus-purified crystalline SCE-2787 was found to be insufficient in solubility for its use as a medicinal chemical to be administered by injection. Accordingly, it is an object of the invention to provide a novel form of SCE-2787 which has satisfactory stability and solubility and can be put into practical use as a medicinal chemical.

The present inventors had made investigations in an attempt to find a form of antimicrobially very active SCE-2787 which has good storage stability and sufficient solubility in water and, if possible, which is in a crystalline form which is advantageous in terms of purification, handling, purity and so on. However, as is often the case with cephalosporins, it had been very difficult to crystallize some forms of SCE-2787 which has sufficient solubility and stability though the present inventors had tried various conditions for crystallization of such stable and water-soluble forms of SCE-2787 over a long period. The present inventors were at last successful in crystallization of SCE-2787 (HCl) and found that the monohydrochloride of SCE-2787 [i.e. SCE-2787(HCl)] unexpectedly has much improved solubility in water and can exist in the form of stable crystals. They further made investigations in search of a method of depriving the crystals thus obtained in the solvate form of the organic solvent they contain and another method of producing crystals of SCE-2787 (HCl) without using any organic solvent and, as a result, unexpectedly found that although it is difficult to achieve solvent removal to a satisfactory extent by ordinary vacuum drying without causing decomposition of the active ingredient, satisfactory solvent removal can be attained by subjecting said crystals to such a special solvent removal technique as supercritical fluid extraction or humidification and also that SCE-2787 (HCl) can be produced by reacting directly SCE-2787 in solid state with gaseous HCl, whereby advantageously the employment of organic solvents accompanied by a step of removing the organic solvents as post-reaction can be avoided. Further investigations based on these findings have now led to completion of the present invention. Thus, the invention is concerned with crystals of 7β-[(Z)-2-(5-amino-1,2,4-thiadiazol-3-yl)-2-methoxyiminoacetamido]-3-(1-imidazo[1,2-b]pyridazinium)methyl-3-cephem-4-carboxylate hydrochloride or a solvate thereof.

The solubility in water of the crystals of SCE-2787(HCl) as obtained in accordance with the invention is not less than 1,000 mg/cc (15° C., pH 1.0–1.9), whereas the solubility of SCE-2787 (crystalline) is about 17 mg/cc (25° C.). It is thus evident that the solubility in water of crystals of SCE-2787 (HCl) can be increased dramatically by conversion to the hydrochloride.

The SCE-2787(HCl) crystals according to the invention can be produced generally by reacting SCE-2787 with hydrogen chloride in the presence of water and an organic solvent, collecting the resulting precipitate crystals and, if desired, subjecting the crystals to organic solvent elimination procedure for conversion to organic solvent-free SCE-2787(HCl) crystals. Either the amorphous form or the crystalline form of SCE-2787 can be used as the starting material.

In originally crystallizing SCE-2787 (HCl) of the present invention, crystals of SCE-2787 were dissolved in dilute hydrochloric acid, and the solution was concentrated to half the volume, whereto dimethylformamide was added. Acetone was gradually added to the mixture under stimulating at room temperature to give the crystals. By reacting hydrogen chloride with SCE-2787, using the thus obtained crystals as a seed crystal, crystallization of SCE-2787 (HCl) has been enabled under a wide variety of conditions.

The starting material in practicing the invention, namely SCE-2787, can be produced in the amorphous form, for example by the procedure described in the above-cited Japanese Kokai Tokkyo Koho No. 62-149682 (EPA Laid-Open No. 203271), in particular in Example 13 therein.

In the method for producing SCE-2787 (HCl) employing organic solvents, SCE-2787 crystals can be produced by dissolving an amorphous powder of SCE-2787 in a small amount of water or by purifying and concentrating such powder in the conventional manner. They can be produced also by neutralizing an aqueous solution of SCE-2787(HCl) with an alkali such as sodium hydrogen carbonate.

Generally, SCE-2787 (amorphous or crystalline) is reacted with one equivalent or more (desirably from the economical viewpoint, up to about 5 equivalents, although there is no upper limit) of hydrogen chloride in the presence of 0.1 part by weight or more (preferably from the economical viewpoint, up to about 10 parts by weight, although there is no upper limit), desirably 1-5 parts by weight of water relative to one part by weight of SCE-2787 and in the presence of about 1 to 10 times the amount of water used of an organic solvent.

As the organic solvent to be used, the hydrophilic organic solvents are preferred. Usable as the organic solvent are, for example, ketones (e.g. acetone), ethers (e.g. tetrahydrofuran), lower alcohols (e.g. methanol, ethanol, etc.), esters (e.g. ethyl acetate, etc.), hydrocarbons (e.g. benzene), amides (e.g. N,N-dimethylformamide), nitriles (e.g. acetonitrile) and halogenated hydrocarbons (e.g. methylene chloride). HCl may be used in the form of an aqueous hydrochloric acid solution or in the form of a solution in any of the solvents mentioned above or, alternatively, gaseous hydrogen chloride may be blown into a solution or suspension of SCE-2787 (crystalline or amorphous) in water or an organic solvent. As another successful way to react HCl with SCE-2787, gaseous hydrogen chloride is reacted directly with SCE-2787 in a solid state. In the above manner, the reaction between SCE-2787 and HCl in the presence of water and an organic solvent or without solvent takes place immediately. The time required for crystallization may vary depending upon the amounts of water, organic solvent and HCl used, among others. For achieving a high yield, it is desirable and preferable to spend about 5 minutes to 24 hours for crystallization.

As a production method using an organic solvent, more preferably, the SCE-2787(HCl) crystals according to the invention can be produced generally by dissolving or suspending SCE-2787 crystals in water and adding hydrogen chloride or hydrochloric acid, or dissolving SCE-2787 directly in hydrochloric acid, then adding an organic solvent to cause crystallization and collecting the resulting crystals by such means as filtration. The organic solvent solvate obtained in that manner can be converted to the organic solvent-free SCE-2787(HCl) crystal form by subjecting said solvate to an adequate organic solvent removal procedure. As mentioned above, it is also a more preferable method to blow gaseous hydrogen chloride to SCE-2787 in a solid state, i.e. without being dissolved or suspended in a solvent. According to the method it is advantageously unnecessary to effect organic solvent removal procedure. More specifically, the method for producing SCE-2787 (HCl) without employing organic solvents can be generally carried out by bringing a gas containing gaseous HCl in a concentration of about 0.01% (by weight, hereinafter w/w percent is meant by "%" unless otherwise specified) to about 3%, preferably about 0.05% to about 2%, into SCE-2787 in a solid state. The preferred gas to be used for diluting HCl gas is exemplified by carbon dioxide or nitrogen. In this method, SCE-2787 in crystalline form is preferably used as the starting material.

As a more preferable method employing an organic solvent, the organic solvent solvates of SCE-2787(HCl) can be prepared in the following manner. In the case of acetone solvate, for instance, SCE-2787 (crystalline) is suspended in ⅓ to 10 parts by weight, desirably ½ to 2 parts by weight, relative to one part by weight of SCE-2787, of water, 1 to 5 equivalent of hydrochloric acid is added for dissolution of SCE-2787 and, then, acetone is added in an amount 2-6 times, preferably 3-5 times, the amount of water used to thereby cause the acetone solvate of SCE-2787(HCl) to crystallize out. The thus-obtained acetone solvate of SCE-2787(HCl) generally contains 0.5 to 1 equivalent of acetone. In the case of ethanol solvate, the ethanol solvate of SCE-2787(HCl) is preferably crystallized out from the above-mentioned hydrochloric acid solution of SCE-2787 with ethanol, which is used in an amount 2-5 times, desirably 2-3 times, the amount of water used in said hydrochloric acid solution. The thus-obtained ethanol solvate of SCE-2787(HCl) generally contains 0.5 to 1.5 equivalent of ethanol. Furthermore, the solvates corresponding to ethanol, methanol, tetrahydrofuran, ethyl acetate, benzene, N,N-dimethylformamide and the like solvents mentioned above can be prepared by stirring the acetone solvate of SCE-2787(HCl), which can be obtained efficiently in the above manner, in the respective organic solvents. Also, the ethanol solvate can be produced by passing the nitrogen gas saturated with ethanol into the acetone solvate.

The solvates of SCE-2787(HCl) thus obtained each shows crystallinity as confirmed by powder X-ray diffraction. The SCE-2787(HCl) solvates obtained have high purity and good stability.

On the other hands, it is desirable that the organic solvent solvates among the solvates obtainable in the above manner should be deprived of the organic solvents prior to their use in pharmaceutical compositions. However, ordinary vacuum drying, for instance, can hardly eliminate the solvents to a satisfactory extent without causing decomposition of SCE-2787(HCl) itself. In accordance with the invention, this problem can be overcome and such solvents can be removed efficiently by using the supercritical fluid extraction method using carbon diode or the like or the humidification method, without increasing the temperature. After solvent removal, the product SCE-2787(HCl) may be dried by a conventional method of drying, such as vacuum drying or air-drying. The SCE-2787 solvates, such as SCE-2787(HCl) acetone solvate or SCE-2787(HCl) ethanol solvate, can be deprived of the solvents by supercritical fluid extraction using, for example carbon dioxide, in the manner mentioned below. Solvent elimination can be effected also by the humidification method by passing humidified air or nitrogen having a relative humidity of 50 to 90%, desirably 60 to 80%, through the solvates in a per se known conventional manner. The thus-obtained SCE-2787(HCl) products show crystallinity as evidenced by powder X-ray diffraction analysis.

The supercritical fluid extraction is carried out by charging an extraction vessel with the cephalosporin compound in the solid form and passing supercritical carbon dioxide through the same either continuously or intermittently to thereby cause the solvent contained in the solid cephalosporin compound to be extracted with supercritical carbon dioxide. The extractor to be used in the practice of the invention is preferably a pressure vessel and generally has a temperature adjusting mechanism. It is necessary that the pressure vessel should be usable at least at the critical pressure of carbon dioxide, namely 75.3 kg/cm$^2$ (absolute pressure), generally within the pressure range of 100 to 500 kg/cm$^2$. The shape of the extractor is not critical. A vertical-type cylindrical vessel equipped with a gas inlet nozzle, a gas outlet nozzle and a nozzle or lid for charging and taking out the solid cephalosporin compound is preferred, however. It is necessary that the extractor should have a mechanism for holding the solid cephalosporin compound therein. Said mechanism can be selected from among various types depending on the grain size and corrosiveness of the solid cephalosporin compound, operability in charging and discharging and economic feature of the equipment. For instance, a system most suited for the purpose can be chosen from the following: a system comprising a perforated plate provided in the bottom portion of the vessel and covered with a filter cloth or wire gauze (e.g. stainless steel wire gauze) for holding said solid compound, a system comprising a porous sintered metal (e.g. stainless steel) or ceramic filter, and a system comprising a cylindrical vessel having a wire gauze (e.g. stainless steel wire gauze) or filter cloth spread on the bottom, which vessel is to be placed in an extractor after filling with the solid cephalosporin compound.

Figure 2:
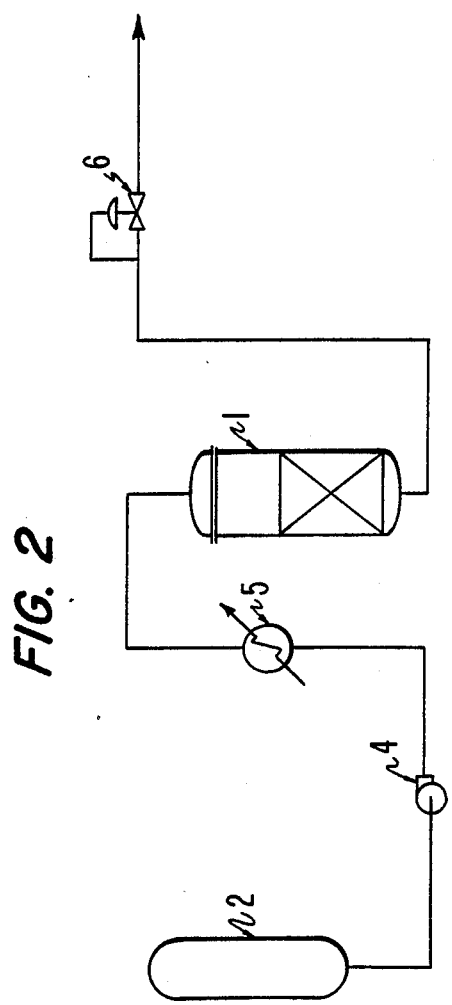

Two examples of the equipment to be used in the practice of the invention, which are most simple, are shown in FIG. 1 and FIG. 2.

FIG. 1 and FIG. 2 are described below.
1—Extractor
2—Carbon dioxide cylinder
3—Condenser
4—High-pressure metering pump
5—Heater
6—Pressure adjusting valve

FIG. 1

Carbon dioxide fed from the carbon dioxide cylinder 2 is liquefied in the condenser 3 and pumped under pressure by means of the high-pressure metering pump 4. It is heated to a prescribed temperature in the heater 5, whereby it is converted to supercritical carbon dioxide, which then enters the extractor 1 filled in advance with the solid cephalosporin compound. The supercritical carbon dioxide comes into contact with the solid cephalosporin compound and extracts the residual solvent therefrom and, thereafter, is exhausted from the apparatus via the pressure-adjusting valve 6.

FIG. 2

Liquefied carbon dioxide is fed from the carbon dioxide cylinder 2 directly to the high-pressure metering pump 4, in which it is pressurized and from which it is pumped to the heater 5 for conversion to supercritical carbon dioxide. The subsequent behavior is the same as described above referring to FIG. 1.

In FIG. 1 and FIG. 2, supercritical carbon dioxide enters the extractor 1 at the top and flows down therethrough. The reverse direction of flow may also be used. In this case, it is preferable to provide a filter in the upper part of the vessel or in the close vicinity of the outlet of the vessel so that loss of the powdery cephalosporin compound and choking up of the piping and/or valve in the exhaustion line can be prevented.

Supercritical carbon dioxide to be used in accordance with the invention should preferably have a temperature not lower than the critical temperature 31.1° C. and a pressure not lower than the critical pressure 75.3 kg/cm$^2$ (absolute pressure).

The temperature of supercritical carbon dioxide to be used in accordance with the invention may be at any level not lower that the critical temperature of carbon dioxide (31.1° C.) but should preferably be within the range of about 35° to about 50° C. from the viewpoint of temperature controllability, heat stability of the cephalosporin compound and so on. The pressure of supercritical carbon dioxide may be at any level not lower than the critical pressure of carbon dioxide (75.3 kg/cm$^2$, absolute pressure) but, from the viewpoints of pressure controllability and economy, among others, should preferably be within the range of about 80–300 kg/cm$^2$ (absolute pressure). The flow rate of supercritical carbon dioxide is not critical but, generally, should suitably be within the range of about 0.5 to 50 kg/hour per kilogram of the solid cephalosporin compound.

Conditions similar to those employed in the conventional solvent removing method by humidification may also be used. Thus, supercritical carbon dioxide may be used in a humidified state, or the moisture content of the solid cephalosporin compound may be adjusted before the solvent removal operation is conducted. For instance, solvent removed may be carried out with supercritical carbon dioxide containing about 0.1 to 5% (w/w %) of water vapor, or after humidifying the solid cephalosporin compound to a moisture content of 5 to 50% (w/w %) based on the yield of cephalosporin compound after drying.

When the cephalosporin compound contains a plurality of solvents, these solvents may be removed simultaneously. The solid cephalosporin compound is preferably used in the form of a powder prepared in advance by grinding.

According to the humidification method, organic solvent removal can be effected in the conventional manner by passing humidified air or nitrogen having a relative humidity of 50 to 90%, desirably 60 to 80%, through the organic solvent solvate of SCE-2787(HCl).

The thus-obtained SCE-2787(HCl) shows crystallinity as evidenced by powder X-ray diffraction analysis.

Figure 11:
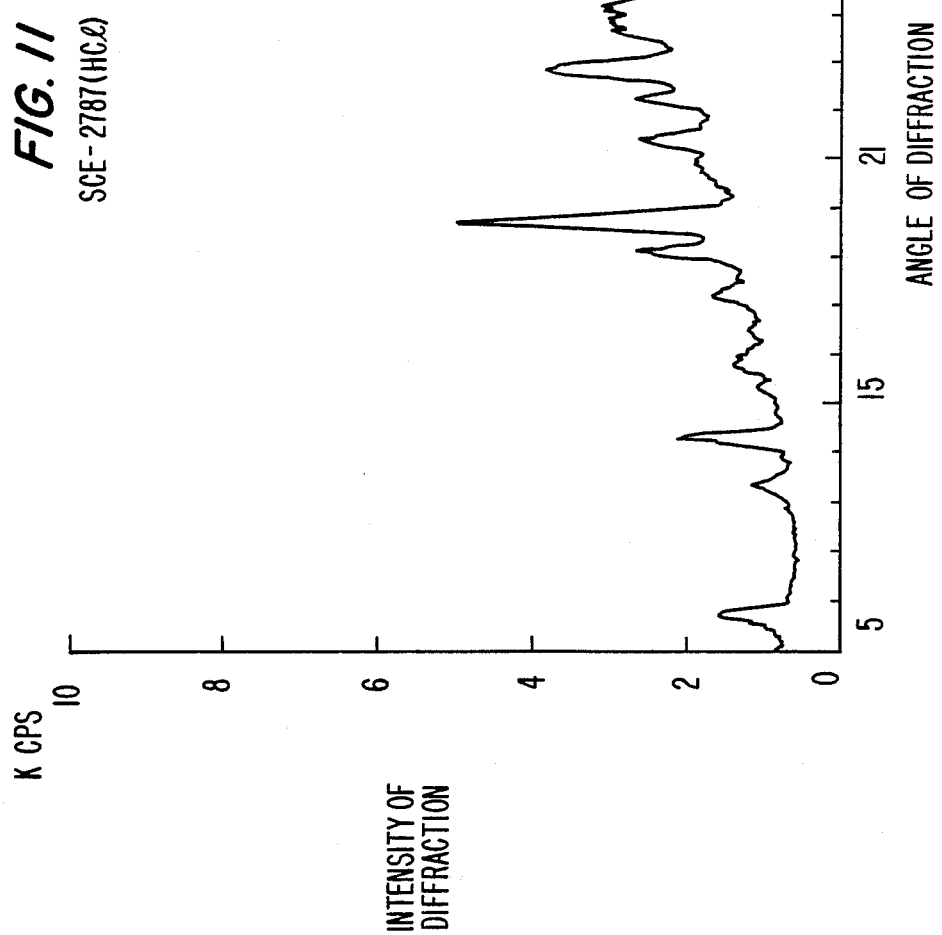

The crystals of SCE-2787(HCl) include, for example, the following three representative crystal forms:

(A): the crystal form having the powder X-ray diffraction pattern shown in FIG. 11 (showing characteristic peaks at lattice spacings (d) of 14.2, 7.4, 4.9, 4.7, 4.1, 3.8, 3.7, 3.5, 3.4, 3.3)

Figure 7:
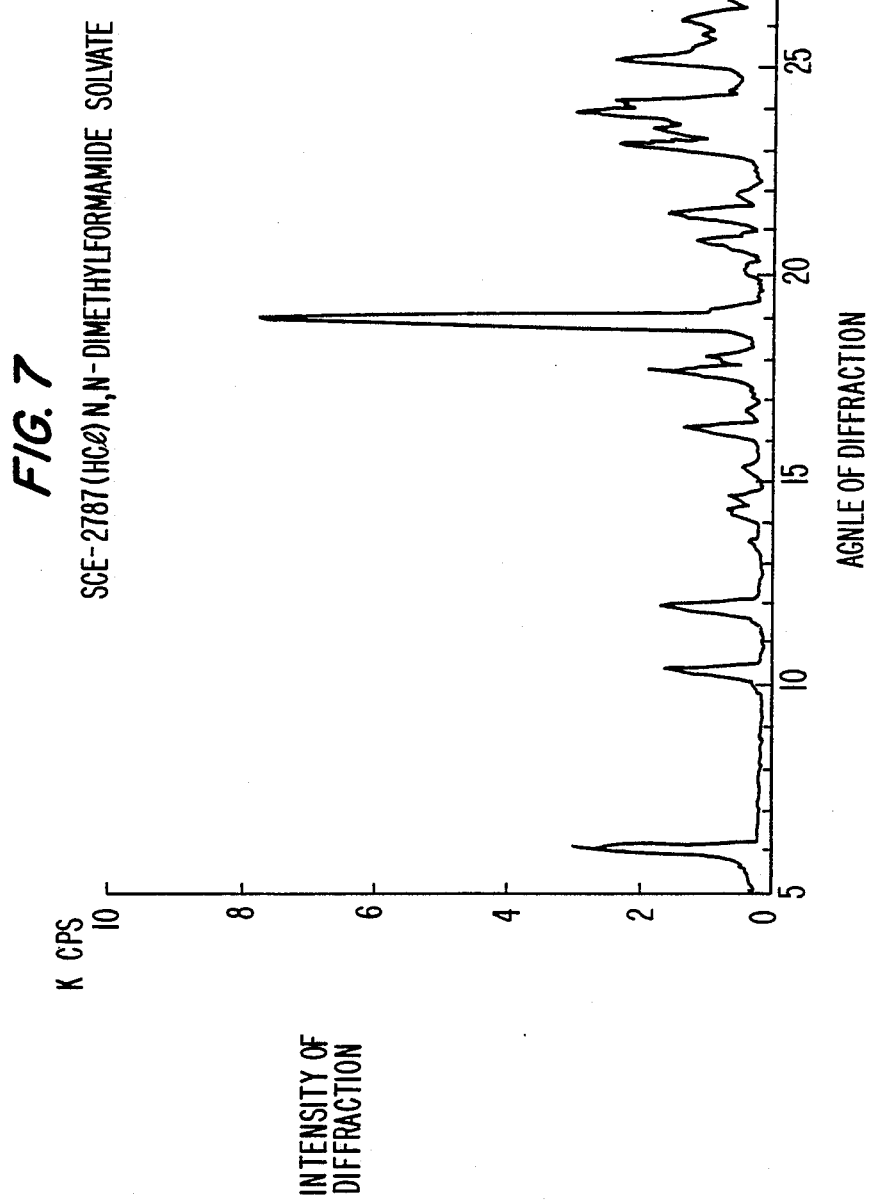
Figure 9:
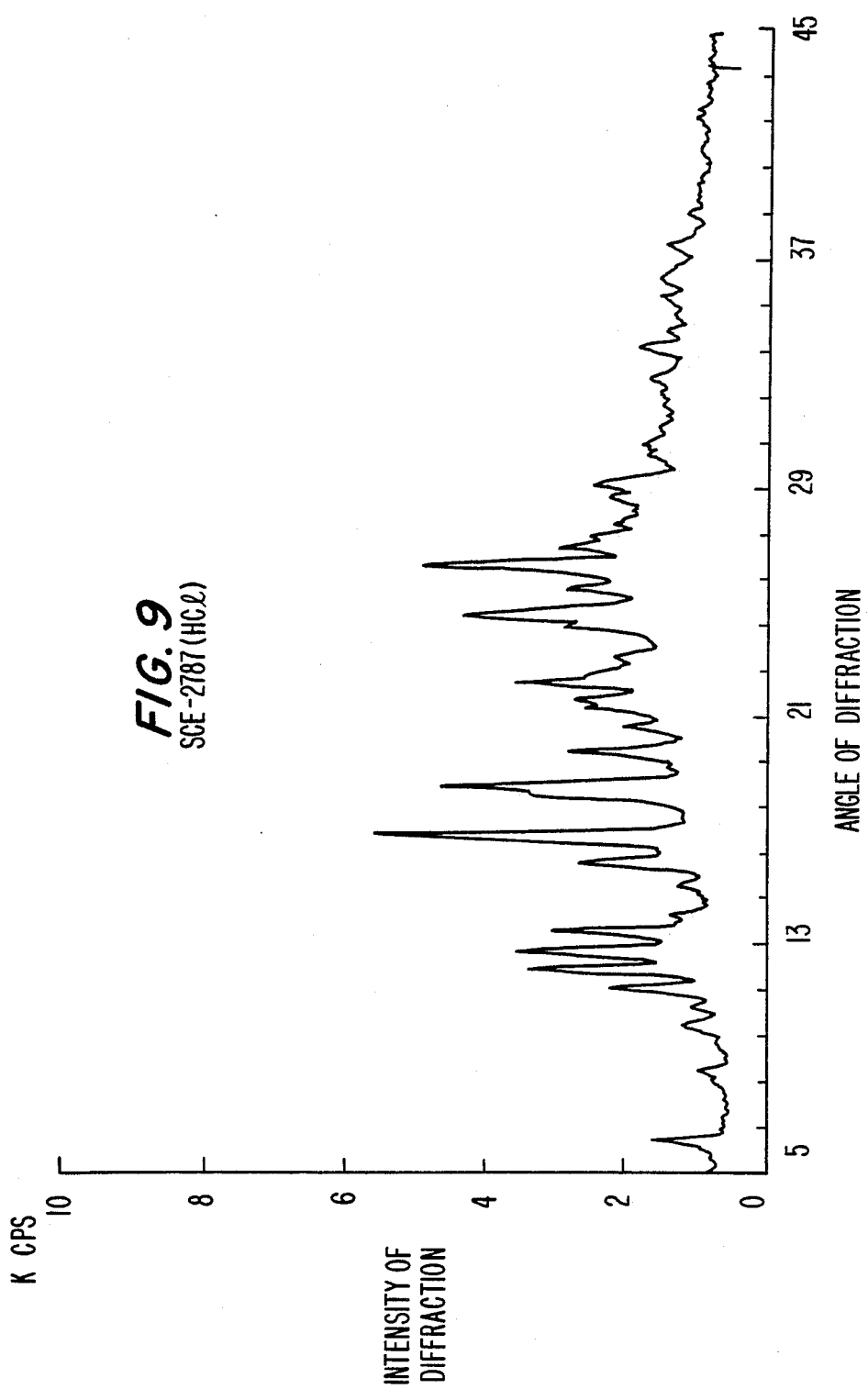

(B): the crystal form having the powder X-ray diffraction pattern as shown in FIG. 7 (showing characteristic peaks at lattice spacings (d) of 8.6, 6.5, 5.4, 4.2, 3.6, 3.4) and (C): the crystal form having the powder X-ray diffraction pattern shown in FIG. 9. (showing characteristic peaks at lattice spacings (d) of 7.3, 7.0, 6.6, 5.3, 4.9, 4.8, 4.0, 3.6, 3.4)

The SCE-2787(HCl) crystals obtained in accordance with the invention can be used as an injectable medicinal chemical and can be made up into pharmaceutical compositions by a conventional method.

The SCE-2787(HCl) crystals according to the invention are superior in stability to the known form of SCE-2787 (amorphous), as illustrated hereafter in the examples. Furthermore, as compared with SCE-2787 (crystalline), they have a markedly improved solubility in water. They are sufficiently free of residual solvents and have high purity and, accordingly, are usable in pharmaceutical compositions.

The following working examples and reference examples illustrate the invention in further detail. It is to be understood, however, that they are by no means limitative of the scope of the present invention.

In the following reference examples, the stability data given are the residual percentages determined by high-performance liquid chromatography after storing under the respective conditions described for the period described.

REFERENCE EXAMPLE 1

Production of SCE-2787 (crystalline) from SCE-2787 (amorphous)

In 400 ml of distilled water was dissolved 100 g of the lyophilized product SCE-2787 (amorphous) obtained by following the procedure described in Japanese Kokai Tokkyo Koho No. 62-149682 (European Patent Appln. Laid-Open No. 203271), Example 13, and crystallization was induced by stirring at room temperature for 1.5 hours. The resultant crystals were collected by filtration, washed with 100 ml of distilled water and dried under reduced pressure to give 77.6 g of SCE-2787 (crystalline).

Elemental analysis:

Calculated for $C_{19}H_{17}N_9S_2O_5.3.3H_2O$: C, 39.69; H, 4.14; N, 21.92; S, 11.15

Found: C, 39.81; H, 3.88; N, 21.92; S, 11.45.

Figure 3:
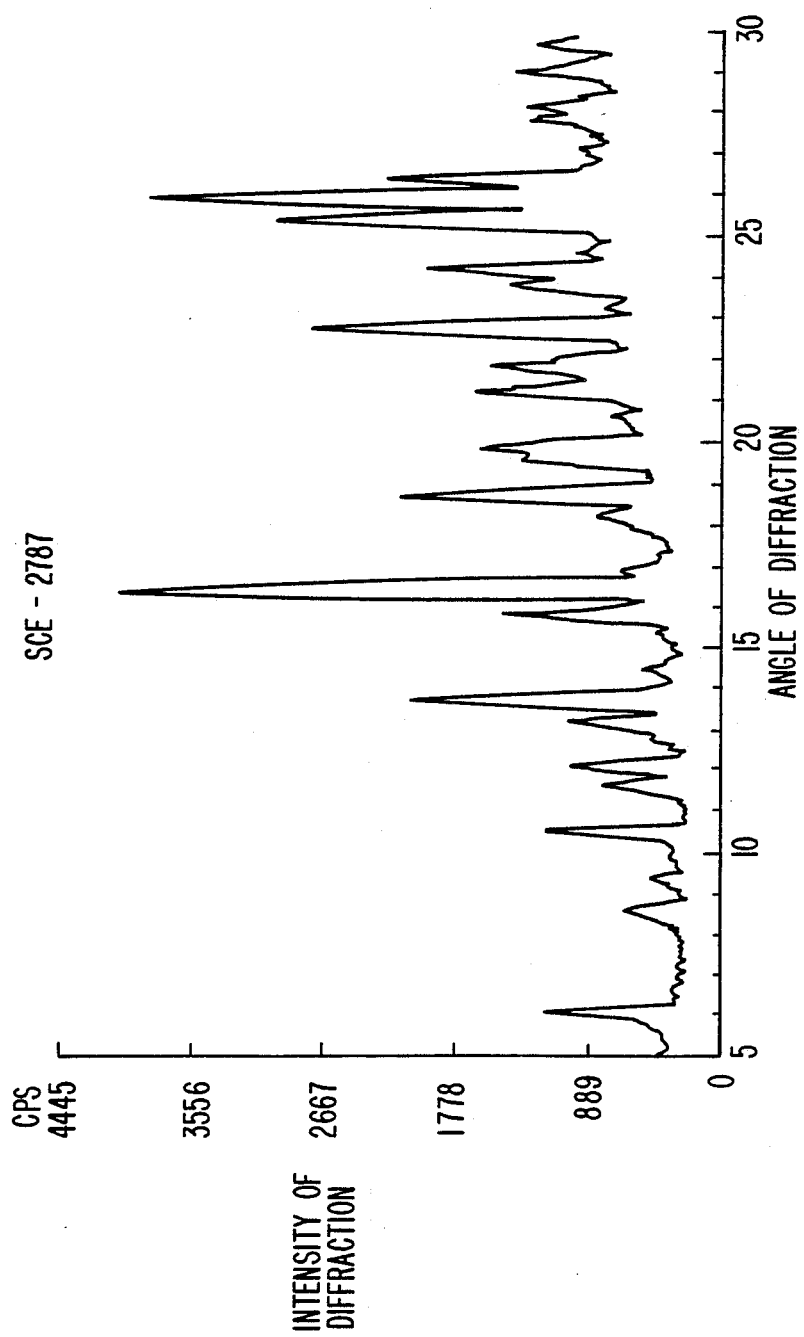

In FIG. 3, a powder X-ray diffraction pattern (CuKα, 40 kV, 100 mA) of this product is shown.

REFERENCE EXAMPLE 2

Production of SCE-2787 (crystalline) from SCE-2787 solution in hydrochloric acid In 300 ml of distilled water was suspended 56.6 g of the SCE-2787 (crystalline) obtained in Reference Example 1. Then, 100 cc of 1N hydrochloric acid was added for causing dissolution of the crystals. The resultant solution was adjusted to pH about 4 with anhydrous sodium carbonate. Crystallization was caused by allowing the mixture to stand at room temperature for 3 hours with occasional shaking. The thus-obtained crystals were washed with 150 ml of distilled water and dried under reduced pressure to give 42.4 g of SCE-2787 (crystalline).

REFERENCE EXAMPLE 3

Production of SCE-2787(HCl) (amorphous)

In 20 ml of distilled water was suspended 515 mg of the SCE-2787 (crystalline) obtained in Reference Example 1, 1 ml of 1N hydrochloric acid was added, and SCE-2787(HCl) (amorphous) was obtained by lyophilization. The moisture content of this product was 3.5%.

Elemental analysis:

Calculated for $C_{19}H_{18}N_9ClO_5S_2.2.5H_2O$: C, 38.22; H, 3.88; N, 21.11; Cl, 5.94

Found C, 38.04; H, 4.05; N, 21.26; Cl, 5.87

The stability of this product as determined after 1 week of storage at 40° C. was 95% in terms of residual percentage.

EXAMPLE 1

Crystals of acetone solvate of SCE-2787(HCl) from SEC-2787

Figure 4:
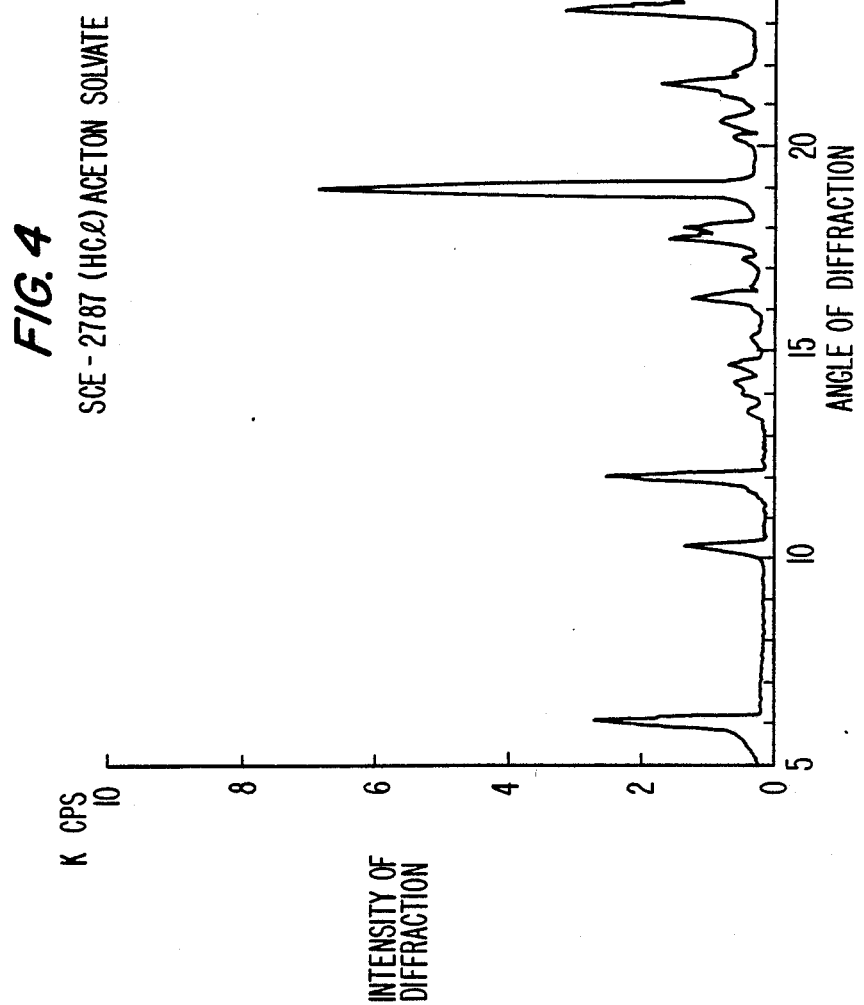

In 20 ml of 1N hydrochloric acid was dissolved 11.3 g of the SCE-2787 (crystalline) obtained in Reference Example 1, then 77 ml of acetone was added slowly with stirring. The resultant mixture was stirred at room temperature for 7 hours to cause crystallization. The resultant crystals were collected by filtration, washed with 20 ml of a mixture of acetone and water (6:1) and further with 40 ml of acetone, and air-dried under blowing to give 7.6 g of acetone-solvates SCE-2787(HCl). In FIG. 4, a powder X-ray diffraction pattern (CuKα, 40 kV, 70 mA) is shown.

This product had a moisture content of 2.6% and an acetone content of 8.0% (0.85 mole). The stability data for this product as determined after 8 days of storage at 40° C. and 60° C. were 98% and 97%, respectively, in terms of residual percentage.

EXAMPLE 2

Crystals of acetone solvate of SCE-2787(HCl) from SCE-2787

In 240 ml of 3N hydrochloric acid was dissolved 138.4 g of the SCE-2787 (crystalline) obtained in Reference Example 1. Acetone (720 ml) was then added slowly with stirring. After seed crystals as obtained in Example 13 mentioned hereafter were added, the resultant mixture was stirred at room temperature for 2 hours for causing crystallization. Furthermore, 360 ml of acetone was added dropwise over 1 hour and, after completion of the dropping, the resultant mixture was stirred for 4 hours for further crystallization. The resultant crystals were collected by filtration, washed with 195 ml of a mixture of acetone and water (6:1) and further with 480 ml of acetone, and dried by exposure to a dried air stream to give 126.6 g of acetone-solvates SCE-2787(HCl). This product had a moisture content of 5.3% and an acetone content of 7.3% (0.8 mole).

EXAMPLE 3

Crystals of ethanol solvate of SCE-2787(HCl) from SCE-2787

In 30 ml of 2N hydrochloric acid was dissolved 11.2 g of the SCE-2787 (crystalline) obtained in Reference Example 1. Ethanol (60 ml) was slowly with stirring, and the resultant mixture was stirred at room temperature for 30 hours to effect crystallization. The resultant crystals were collected by filtration and washed with 50 ml of a mixture of ethanol and water 4:1). After further washing with 50 ml of ethanol, the crystals were dried by exposure to a dried air stream to give 5.8 g of ethanol-solvates SCE-2787(HCl). This product had a moisture content of 4.8% and an ethanol content of 8.6% (1.2 moles).

Figure 5:
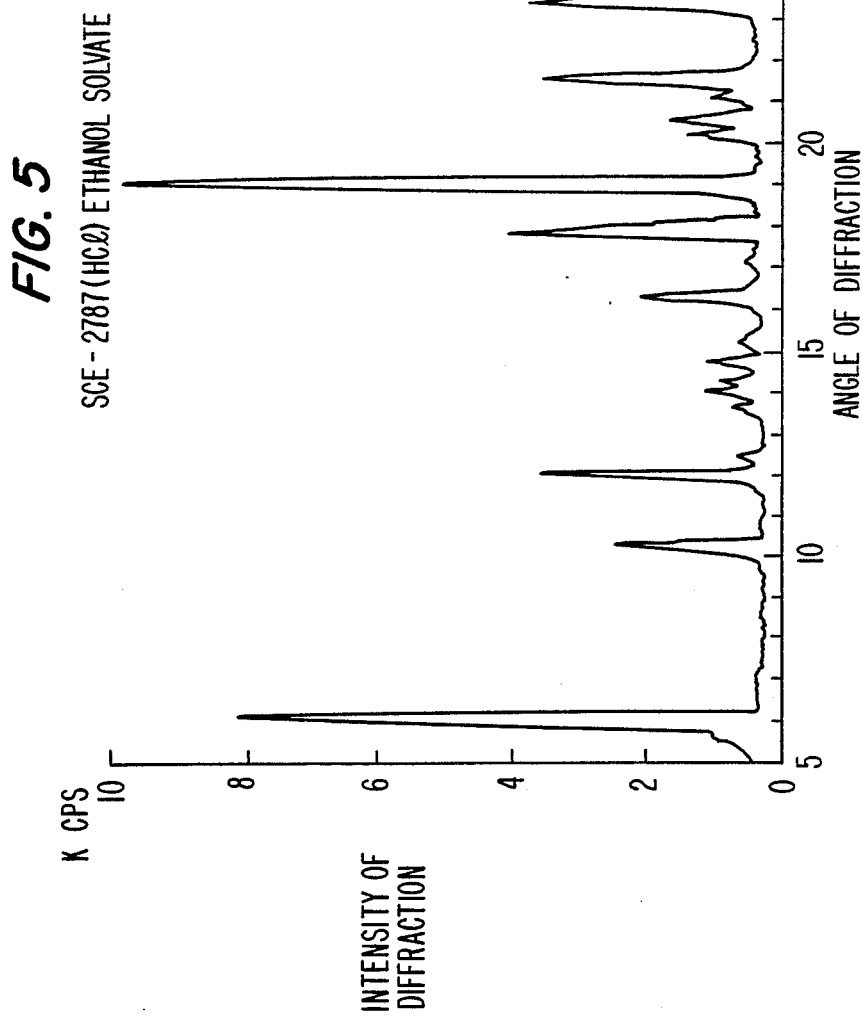

In FIG. 5, a powder X-ray diffraction pattern (CuKα, 40 kV, 100 mA) of this product is shown.

EXAMPLE 4

Crystals of ethanol solvate of SCE-2787(HCl) from acetone solvate of SCE-2787

In 30 ml of ethanol was suspended 3.0 g of the acetone-solvates SCE-2787(HCl) obtained in Example 2, and the suspension was stirred for 4.5 hours. The resultant crystals were collected by filtration, washed with 35 ml of ethanol, dried by exposure to a dried air stream and further dried under reduced pressure to give 2.8 g of ethanol-solvates SCE-2787(HCl). This product had a moisture content of 3.0% and an ethanol content of 7.5% (1.0 mole). NMR spectrometry of this product failed to demonstrate the presence of acetone. The stability data for this product as determined after 8 days of storage at 40° C. and 60° C. were 98% and 98%, respectively, in terms of residual percentage.

EXAMPLE 5

Crystals of methanol solvate of SCE-2787(HCl) from acetone solvate of SCE-2787(HCl)

A suspension of 1 g of the acetone-solvates SCE-2787(HCl) obtained in Example 2 in 10 ml of methanol was stirred at room temperature for 6 hours. The crystals thus obtained were washed with 5 ml of methanol and dried by exposure to a dried air stream to give 890 mg of methanol-solvates of SCE-2787 (HCl). This product had a moisture content of 3.1%. NMR spectroscopy revealed that the methanol content was about 1 mole and that acetone was absent.

Figure 6:
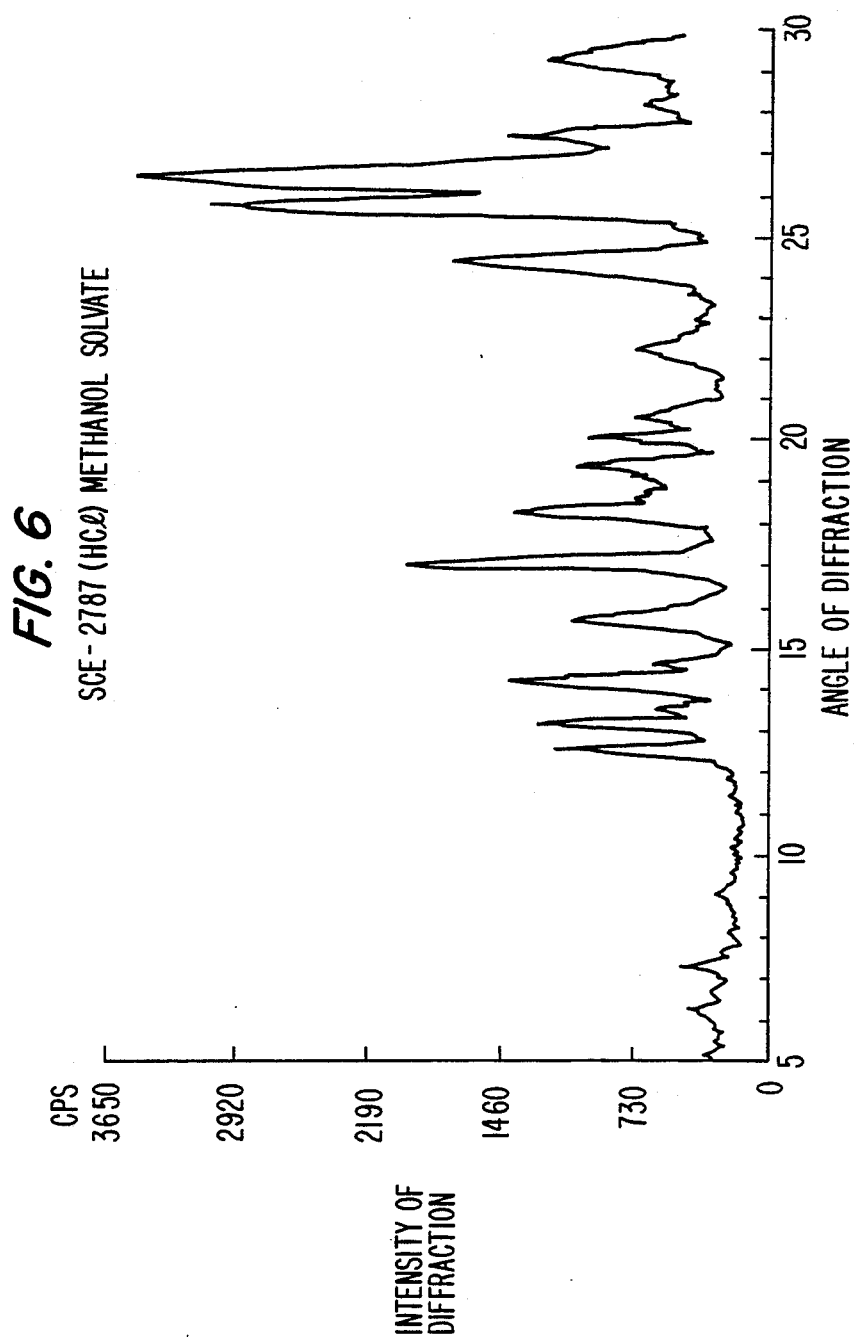

In FIG. 6, a powder X-ray diffraction pattern (CuXα, 40 kV, 70 mA) of this product is shown.

EXAMPLE 6

Crystals of N,N-dimethylformamide solvate of SCE-2787(HCl) from acetone solvate of SCE-2787(HCl)

A suspension of 1 g of the acetone-solvates SCE-2787(HCl) obtained in Example 2 in 10 ml of N,N-dimethylformamide was stirred at room temperature for 6 hours. The crystals thus obtained were washed with 5 ml of N,N-dimethylformamide and dried by exposure to a dried air stream to give 625 mg of N,N-dimethylformamide-solvates SCE-2787(HCl). This product had a moisture content of 2.3%. NMR spectroscopy showed that about 1 mole of N,N-dimethylformamide was contained in the product. The presence of acetone was not indicated.

In FIG. 7, a powder X-ray diffraction pattern (CuXα, 40 kV, 70 mA) is shown.

EXAMPLE 7

Solvent removal from acetone solvate of SCE-2787(HCl) by supercritical fluid extraction The acetone-solvates SCE-2787(HCl) obtained in Example 2 was charged into a vertical-type cylindrical vessel having a diameter of 25 mm and a height of 50 mm and equipped in the lower part thereof with a filter plate. Extractive removal of acetone was effected by passing carbon dioxide through the powder layer from the top to the bottom of the vessel (flow rate: 2 liters per minute, on the standard conditions basis) while the vessel outside temperature and the fluid inlet temperature were adjusted to 40° C. and the pressure within the vessel was adjusted to 200 kg/cm$^2$. (The equipment shown in FIG. 1 was used.)

The product had a moisture content of 3.7%. Gas chromatography indicated that the content of residual acetone was 0.5%.

II(KBr)cm$^{-1}$: 1787

NMR (DMSO-d$_6$): 3.48 (2H, dd, J=26.1, 18.9 Hz), 3.87 (3H, s), 5.17 (1H, d, J=5.4 Hz), 5.50 (2H, broad s), 5.85 (1H, dd, J=9.0, 5.4 Hz), 8.04 (1H, dd, J=9.0, 4.5 Hz), 8.41 (1H, d, J=1.8 Hz), 8.41 (1H, d, J=1.8 Hz), 8.85 (1H, d, J=1.8 Hz), 8.98 (1H, d, J=9.0 Hz), 9.11 (1H, d, J=4.5 Hz)

Figure 8:
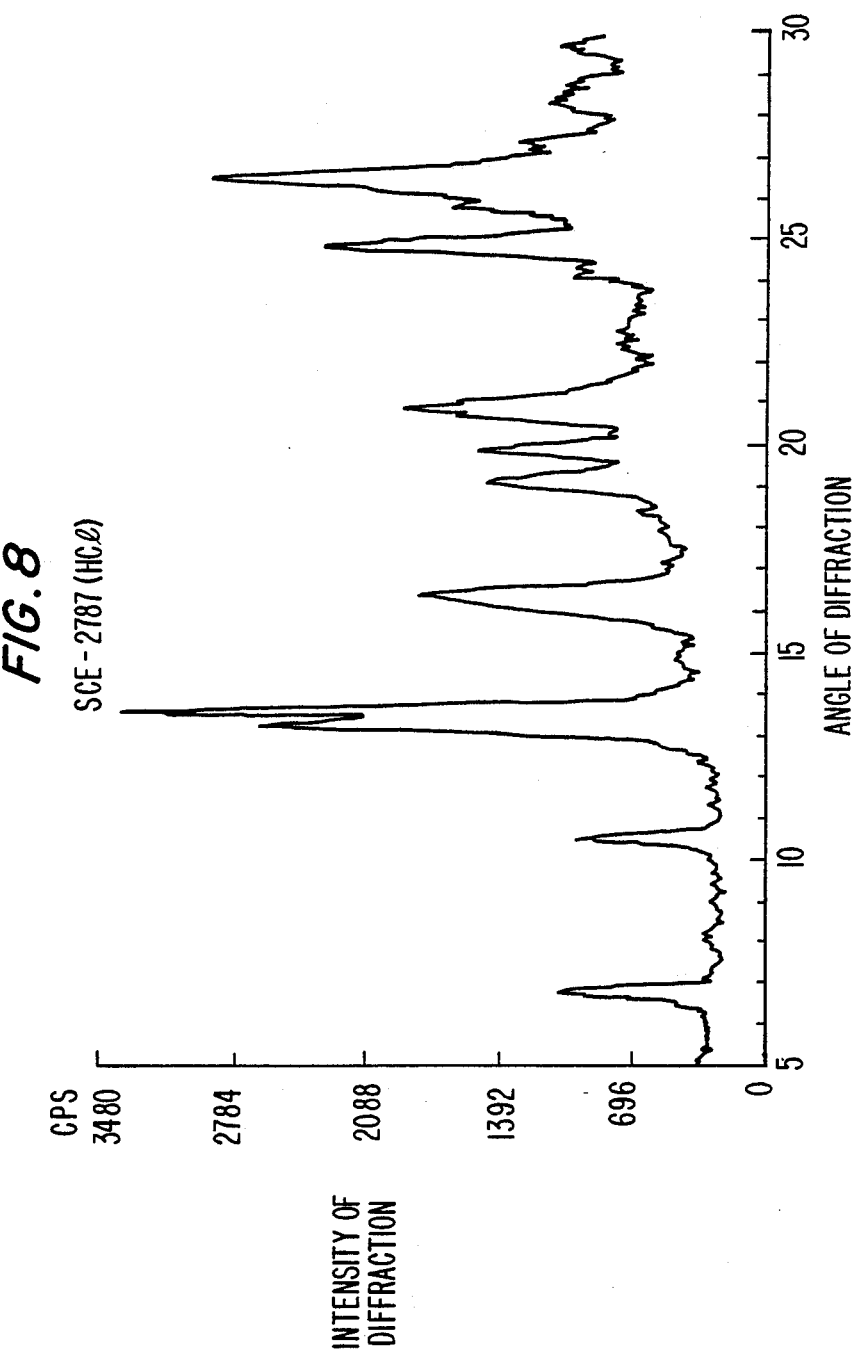

In FIG. 8, a powder X-ray diffraction pattern (CuXα, 40 kV, 70 mA) is shown.

EXAMPLE 8

Solvent removal from ethanol solvate of SCE-2787(HCl) by supercritical fluid extraction Four grams of the ethanol solvate of SCE-2787(HCl) as obtained in Example 3 was subjected to solvent removal in the same manner as in Example 7 to give 3.5 g of SCE-2787(HCl). This product had a moisture content of 2.7%. Gas chromatography indicated that the content of residual ethanol was 0.1% or less. This product gave an NMR spectrum which was substantially the same as that obtained with the product of Example 7. The stability data for said product as determined after 3 weeks of storage at 40° C. and 60° C. were 98%, and 94%, respectively, in terms of residual percentage.

EXAMPLE 9

Organic solvent removal from acetone solvate of SCE-2787(HCl) by humidification

A 5.0-g portion of the acetone solvate of SCE-2787(HCl) as obtained in Example 2 was spread over a glass filter, and solvent removal was effected by passing through the filter and solvate layer a stream of air humidified by passing through a water layer maintained at 10° C. (flow rate: 1 liter per minute). The solvent removal product was then dried under reduced pressure to give 4.85 g of SCE-2787(HCl). This product had a moisture content of 8.2%. NMR spectroscopy revealed that the content of residual acetone was not more than 0.2%. This product gave an NMR spectrum which was essentially the same as that obtained in Example 7.

Elemental analysis:

Calculated for $C_{19}H_{18}N_9ClO_5S_2 \cdot 2.5H_2O$: C, 38.22; H, 3.88; N, 21.11; Cl, 5.94

Found: C, 38.17; H, 3.56; N, 21.02; Cl, 5.96

EXAMPLE 10

Solvent removal from ethanol solvate of SCE-2787(HCl) by humidification

A 4.0-gram portion of the ethanol solvate of SCE-2787(HCl) as obtained in Example 4 was placed on a glass filter and deprived of the solvent by passing through the filter and solvate layer a stream of air humidified by passing through a saturated aqueous solution of sodium acetate to give 3.0 g of SCE-2787(HCl). Gas chromatography showed that this product had a residual ethanol content of 0.1% or less. The thus-obtained SCE-2787(HCl) was dried under reduced pressure. The dried product was tested for its stability under various moisture conditions. The residual percentage data obtained after 1 week or 5 weeks of storage at 40° C. or 60° C. are shown below in the table.

| Moisture | After 1 week | | After 5 weeks | |
| content | 40° C. | 60° C. | 40° C. | 60° C. |
| --- | --- | --- | --- | --- |
| 2.9% | 97% | 96% | 97% | 92% |
| 1.6% | 100% | 98% | 98% | 94% |
| 0.8% | 99% | 97% | 98% | 95% |

EXAMPLE 11

Conversion of crystals of SCE-2787 to crystals of SCE-2787(HCl) using HCl gas diluted in nitrogen Crystals of SCE-2787 (2.5 g, moisture content 2.4%) as produced in accordance with Reference Example 1 were filled in a vertical-type cylindrical glass filter of 25 mm in diameter. Through the layer of the crystals was passed from the upper side of the vessel vertically for 25 hours a stream of 0.1% HCl gas which was prepared by mixing 1% HCl gas (diluted in nitrogen) at the flow rate of 200 ml/min, and nitrogen gas at the flow rate of 1,800 ml/min and then was passed through a U-shaped tube filled with calcium chloride for drying to give crystals of SCE-2787(HCl). The thus-obtained crystals were further exposed to nitrogen gas flow for 11 hours to give crystals of SCE-2787(HCl) showing the powder X-ray diffraction pattern (CuXα, 50 kV, 100 mA) as shown in FIG. 9.

EXAMPLE 12

Figure 10:
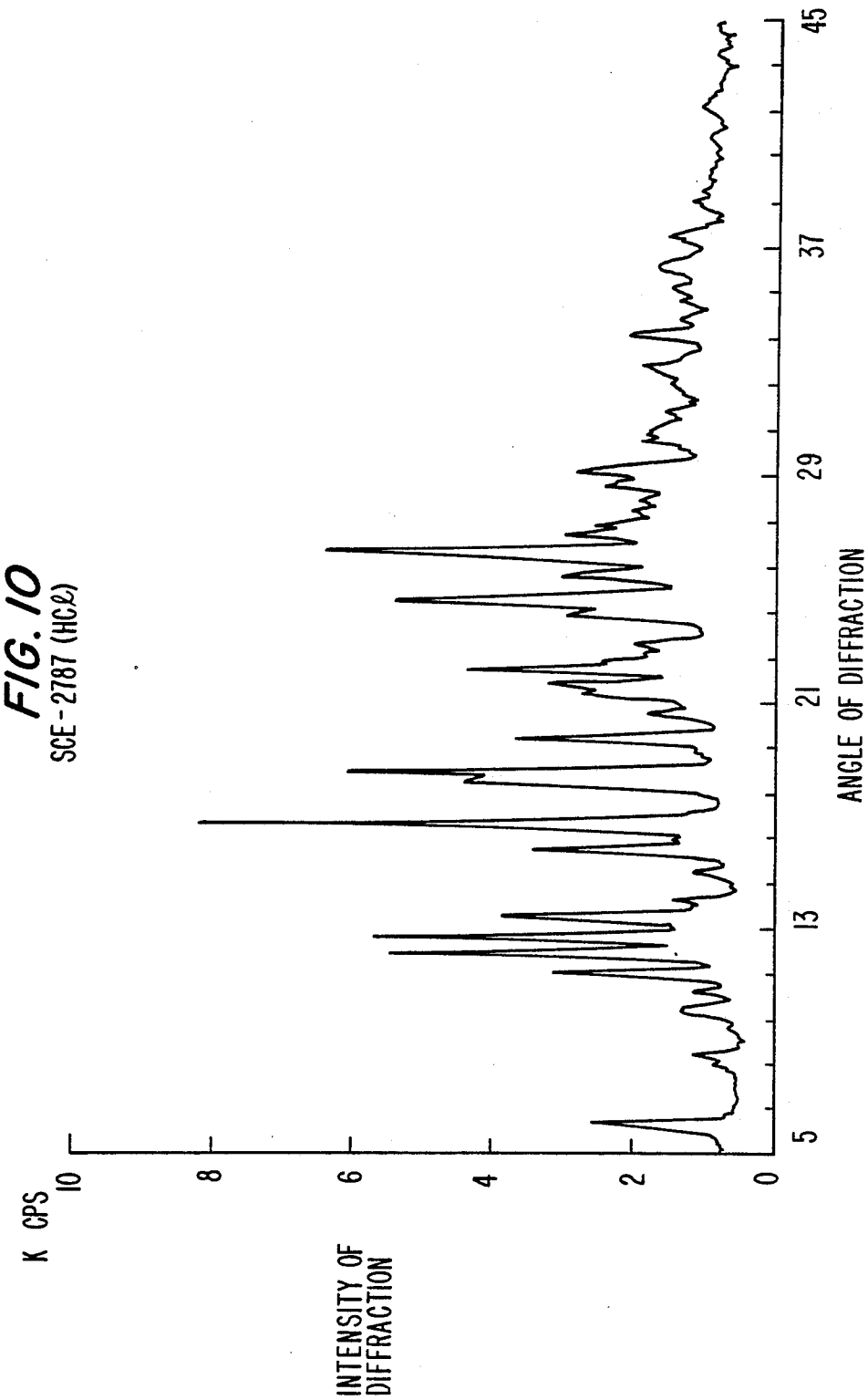

Conversion of crystals of SCE-2787 to crystals of SCE-2787 (HCl) using HCl gas diluted in carbon dioxide Crystals of SCE-2787 (2.5 g, moisture content 9.1%) as produced in accordance with Reference Example 1 were filled in the same glass as Example 11. Through the layer of the crystals was passed from the upper side of the vessel vertically for 20 hours a stream of 0.1% HCl gas which was prepared by mixing 1% HCl gas (diluted in nitrogen) at the flow rate of 800 ml/min and carbon dioxide gas at the flow rate of 7,200 ml/min and then was passed through a U-shaped tube filled with calcium chloride for drying to give crystals of SCE-2787(HCl). The thus-obtained crystals were further exposed to carbon dioxide gas flow for 12 hours to give crystals of SCE-2787(HCl) showing the powder X-ray diffraction pattern (CuXa, 50 kV, 100 mA) as shown in FIG. 10. This product contained 3.6% moisture and 1.0 mol HCl.

EXAMPLE 13

In 1 ml of 1N-HCl was dissolved 563 mg of SCE-2787 (crystalline), and the solution was concentrated under reduced pressure to half the volume. N,N-Dimethylformamide (1 ml) was added to the residue, which dissolved. While the solution was being stimulated with a spatula, 5 ml of acetone was added to the solution dropwise slowly. Continual stimulus charged to the solution at room temperature caused slowly crystallization. Observation with polarizing microscope indicated that this product had crystallinity. On the other hand, 563 mg of SCE-2787 (crystals) was dissolved in 1N-HCl, and 4 ml of acetone was added slowly to the solution with stirring. Addition of the crystals as obtained above as the seed crystals to the mixture at room temperature caused gradual crystallization. The resulting crystals were collected by filtration under reduced pressure, and the collected crystals were washed with acetone and dried under reduced pressure to give 280 mg of the crystals of SCE-2787(HCl) as the acetone solvate. This product had a moisture content of 2.6% and an acetone content of 8.0%.

EXAMPLE 14

Solvent removal from ethanol solvate of SCE-2787(HCl) by humidification

A 3.0-gram portion of the crystals of the ethanol solvate of SCE-2787(HCl) (ethanol content: 9.9%, moisture content: 0.83%), as produced in accordance with the method analogous to that of Example 4, was placed on a vertical-type cylindrical glass filter of 25 mm in diameter and deprived of the solvent by passing through the filter and solvate layer a stream of nitrogen gas humidified by passing through a water layer at 18° C., for 3 hours to give 3.0 g of the crystals of SCE-2787(HCl) showing a powder X-ray diffraction pattern (CuXa, 50 kV, 100 mA) as shown in FIG. 11. This product had a moisture content of 13.7%, and gas chromatography showed that the content of the residual ethanol was not more than 0.01%.

What is claimed is:

1. Crystalline 7β-[(Z)-2-(5-amino-1,2,4-thiadiazol-3-yl)-2-methoxyiminoacetamido]-3-(1-imidazo[1,2-b]-pyridazinium)methyl-3-cephem-4-carboxylate hydrochloride or a crystalline solvate thereof.

2. A process for producing 7β-[(Z)-2-(5-amino-1,2,4-thiadiazol-3-yl)-2-methoxyiminoacetamido]-3-(1-imidazo[1,2-b]-pyridazinium)methyl-3-cephem-4-carboxylate hydrochloride or a solvate thereof, which comprises reacting 7β-[(Z)-2-(5-amino-1,2,4-thiadiazol-3-yl)-2-methoxyiminoacetamido]-3-(1-imidazo[1,2-b]-pyridazinium)methyl-3-cephem-4-carboxylate with hydrogen chloride in a medium comprising water and a hydrophilic organic solvent and collecting the resultant crystals.

3. A process as claimed in claim 2 wherein the collected crystals are further subjected to desolvation of the organic solvent.

4. A process for producing 7β-[(Z)-2-(5-amino-1,2,4-thiadiazol-3-yl)-2-methoxyiminoacetamido]-3-(1-imidazo[1,2-b]-pyridazinium)methyl-3-cephem-4-carboxylate hydrochloride or a solvate thereof, which comprises reacting 7β-[(Z)-2-(5-amino-1,2,4-thiadiazol-3-yl)-2-methoxyiminoacetamido]-3-(1-imidazo[1,2-b]-pyridazinium)methyl-3-cephem-4-carboxylate in a solid state with gaseous hydrogen chloride.

5. A process as claimed in claim 2 wherein the organic solvent is acetone or ethanol.

6. A process as claimed in claim 2 wherein the desolvation is carried out by a humidification method in which humidified air or nitrogen is passed through the organic solvent solvate of the hydrochloride.

7. A process as claimed in claim 2 wherein the desolvation is carried out by a supercritical fluid extraction method.

8. Crystalline 7β-[(Z)-2-(5-amino-1,2,4-thiadiazol-3-yl)-2-methoxyiminoacetamido]-3-(1-imidazo[1,2-b]-pyridazinium)methyl-3-cephem-4-carboxylate hydrochloride of claim 1 having characteristic peaks at lattice spacings (d) of 14.2, 7.4, 4.9, 4.7, 4.1, 3.8, 3.7, 3.5, 3.4, 3.3 in its powder X-ray diffraction pattern.

9. Crystalline 7β-[(Z)-2-(5-amino-1,2,4-thiadiazol-3-yl)-2-methoxyiminoacetamido]-3-(1-imidazo[1,2-b]-pyridazinium)methyl-3-cephem-4-carboxylate hydrochloride of claim 1 having characteristic peaks at lattice spacings (d) of 8.7, 6.5, 5.4, 4.2, 3.6, 3.4 in its powder X-ray diffraction pattern.

10. Crystalline 7β-[(Z)-2-(5-amino-1,2,4-thiadiazol-3-yl)-2-methoxyiminoacetamido]-3-(1-imidazo[1,2-b]-pyridazinium)methyl-3-cephem-4-carboxylate hydrochloride of claim 1 having characteristic peaks at lattice spacings (d) of 7.3, 7.0, 6.6, 5.3, 4.9, 4.8, 4.0, 3.6, 3.4 in its powder X-ray diffraction pattern.

* * * * *